United States Patent
Iwata et al.

(10) Patent No.: US 8,466,441 B2
(45) Date of Patent: Jun. 18, 2013

(54) PARTICLE BEAM THERAPY SYSTEM

(75) Inventors: Takaaki Iwata, Tokyo (JP); Kengo Sugahara, Tokyo (JP); Hisashi Harada, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 90 days.

(21) Appl. No.: 13/258,240

(22) PCT Filed: Feb. 17, 2011

(86) PCT No.: PCT/JP2011/053367
§ 371 (c)(1),
(2), (4) Date: Sep. 21, 2011

(87) PCT Pub. No.: WO2012/111125
PCT Pub. Date: Aug. 23, 2012

(65) Prior Publication Data
US 2012/0211667 A1    Aug. 23, 2012

(51) Int. Cl.
*A61N 5/10*    (2006.01)
(52) U.S. Cl.
USPC .................................................. 250/492.3
(58) Field of Classification Search
USPC ......................... 250/396 R–396 ML, 492.3
See application file for complete search history.

(56) References Cited

U.S. PATENT DOCUMENTS

| | | | |
|---|---|---|---|
| 2006/0231775 A1 * | 10/2006 | Harada | 250/492.3 |
| 2008/0067405 A1 * | 3/2008 | Nihongi et al. | 250/398 |
| 2011/0260074 A1 * | 10/2011 | Honda et al. | 250/396 R |

FOREIGN PATENT DOCUMENTS

| | | | |
|---|---|---|---|
| JP | 2857598 B2 | | 2/1999 |
| JP | 2002-058750 A | | 2/2002 |
| JP | 3458481 | * | 10/2003 |
| JP | 2007-132902 A | | 5/2007 |
| JP | 4532606 B1 | | 8/2010 |
| WO | WO 02/13908 A2 | | 2/2002 |

OTHER PUBLICATIONS

International Search Report (PCT/ISA/210) issued on Mar. 29, 2011, by Japanese Patent Office as the International Searching Authority for International Application No. PCT/JP2010/053367.

* cited by examiner

*Primary Examiner* — Jack Berman
*Assistant Examiner* — Eliza Osenbaugh-Stewart
(74) *Attorney, Agent, or Firm* — Buchanan Ingersoll & Rooney PC

(57) ABSTRACT

The objective is to eliminate the effect of the hysteresis of a scanning electromagnet and resume high-accuracy beam irradiation from an irradiation position where it has been interrupted, even in the case where emergency-stop processing is performed during therapy. There are provided an irradiation management apparatus that controls a scanning electromagnet; and an interlock information inputting device that generates an interlock signal for stopping irradiation of the charged particle beam, when a contingency occurs. When irradiation of the charged particle beam is resumed, the irradiation management apparatus performs idle operation in which the scanning electromagnet is controlled, with the charged particle beam unirradiated, from a start step, which is situated prior to a stop step and is different from the initial step in actual irradiation, to the stop step, and then irradiates the charged particle beam from the desired irradiation position coordinates corresponding to the stop step.

19 Claims, 11 Drawing Sheets

PARTICLE BEAM THERAPY SYSTEM

TECHNICAL FIELD

The present invention relates to a particle beam therapy system utilized in the medical field and R&Ds and particularly to a particle beam therapy system of a scanning type such as a spot-scanning type or a raster-scanning type.

BACKGROUND ART

In general, a particle beam therapy system is provided with a beam generation apparatus that generates a charged particle beam; an accelerator that is connected with the beam generation apparatus and accelerates a generated charged particle beam; a beam transport system that transports a charged particle beam that is accelerated by the accelerator so as to gain predetermined energy and then emitted; and a particle beam irradiation apparatus, disposed at the downstream side of the beam transport system, for irradiating a charged particle beam onto an irradiation subject, which is a diseased site of a patient or the like. Particle beam irradiation apparatuses are roughly divided into apparatuses utilizing a broad irradiation method in which a charged particle beam is enlarged in a dispersion manner by a scatterer, and the shape of the enlarged charged particle beam is made to coincide with the shape of an irradiation subject in order to form an irradiation field; and apparatuses utilizing a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

Patent Document 1 discloses the following invention whose objective is to reduce the effect of the hysteresis of a scanning electromagnet for scanning a charged particle beam and to realize high-accuracy beam irradiation. The invention disclosed in Patent Document 1 includes an irradiation management apparatus that controls a scanning electromagnet, based on the desired irradiation position coordinates of a charged particle beam, and a position monitor that measures the measured position coordinates of the charged particle beam. The irradiation management apparatus is provided with a command value generator that outputs a control input to the scanning electromagnet, based on the desired irradiation position coordinates and correction data generated on the basis of the measured position coordinates, measured by the position monitor in preliminary irradiation in which the excitation pattern of the scanning electromagnet is the same as that of a actual irradiation plan, and the desired irradiation position coordinates.

Accordingly, in the invention disclosed in Patent Document 1, the scanning-electromagnet excitation pattern of the preliminary irradiation is the same as that of the planned actual irradiation, and the control input to the scanning electromagnet is preliminarily corrected based on the result obtained in the preliminary irradiation; therefore, the effect of the hysteresis of the scanning electromagnet is eliminated, so that high-accuracy beam irradiation can be realized.

PRIOR ART REFERENCE

Patent Document

[Patent Document 1] Japanese Patent No. 4532606 (FIGS. 1 and 2)

DISCLOSURE OF THE INVENTION

Problems to be Solved by the Invention

In the invention disclosed in Patent Document 1, correction is preliminarily performed based on the preliminary irradiation, the scanning-electromagnet excitation pattern for which is the same as that for actual irradiation; therefore, there is demonstrated an extra effect that high-accuracy beam irradiation is realized in the actual irradiation. It is true that when therapy is implemented normally, the invention disclosed in Patent Document 1 poses no problem. However, in a therapy scene, due to a contingency where the size of a charged particle beam exceeds the tolerance range or a patient gets sick, there may occur a situation in which irradiation needs to be interrupted, i.e., emergency-stop processing for the particle beam therapy system needs to be implemented.

In this case, emergency-stop processing is implemented so as to temporarily stop irradiation of a charged particle beam. Because the diseased site has partly been irradiated with a charged particle beam, it is required that the irradiation of a charged particle beam is resumed from an irradiation position where it has been interrupted, thereby giving a dose planed through a treatment plan to the whole diseased site. In this situation, provided the irradiation is resumed simply from the irradiation position where it has been interrupted, the irradiation pattern of the scanning electromagnet is resumed from the middle thereof. As a result, because the hysteresis affects the scanning electromagnet, the state of the scanning electromagnet at a time when the irradiation is interrupted differs from the state thereof at a time when the irradiation is not interrupted; thus, there has been a problem that while the state of the scanning electromagnet is left different, the actual irradiation is resumed, a charged particle beam is irradiated onto a position that is different from the position at a time when the irradiation is not interrupted, and hence high-accuracy beam irradiation cannot be performed.

The present invention has been implemented in order to solve the foregoing problems; the objective thereof is to obtain a particle beam therapy system that eliminates the effect of the hysteresis of a scanning electromagnet and can resume high-accuracy beam irradiation from an irradiation position where it has been interrupted.

Means for Solving the Problems

There are provided an irradiation management apparatus that controls a scanning electromagnet, based on desired irradiation position coordinates of a charged particle beam; and an interlock information inputting device that generates an interlock signal for stopping irradiation of the charged particle beam, when a contingency occurs. The irradiation management apparatus is provided with a command value generator that outputs a control input to the scanning electromagnet; and a stop step storage memory that stores a stop step corresponding to the desired irradiation position coordinates at which irradiation of the charged particle beam stops, when the interlock signal is generated by the interlock information inputting device. When irradiation of the charged particle beam is resumed, the irradiation management apparatus performs idle operation in which the scanning electromagnet is controlled, with the charged particle beam unirradiated, from a start step, which is situated prior to the stop step and is different from the initial step corresponding to the initial desired irradiation position coordinates in actual irradiation, to the stop step, and then irradiates the charged particle beam from the desired irradiation position coordinates corresponding to the stop step.

Advantage of the Invention

In the case where emergency-stop processing is performed during therapy, a particle beam therapy system according to the present invention carries out idle operation, based on irradiation command data including a control input to the scanning electromagnet, from a start step, which is situated prior to the stop step and is different from the initial step, and starts beam irradiation from an irradiation position where the irradiation has been interrupted; therefore, the effect of the hysteresis of the scanning electromagnet is eliminated, so that high-accuracy beam irradiation can be resumed from the irradiation position where the irradiation has been interrupted.

BEST MODE FOR CARRYING OUT THE INVENTION

Embodiment 1

Figure 1:
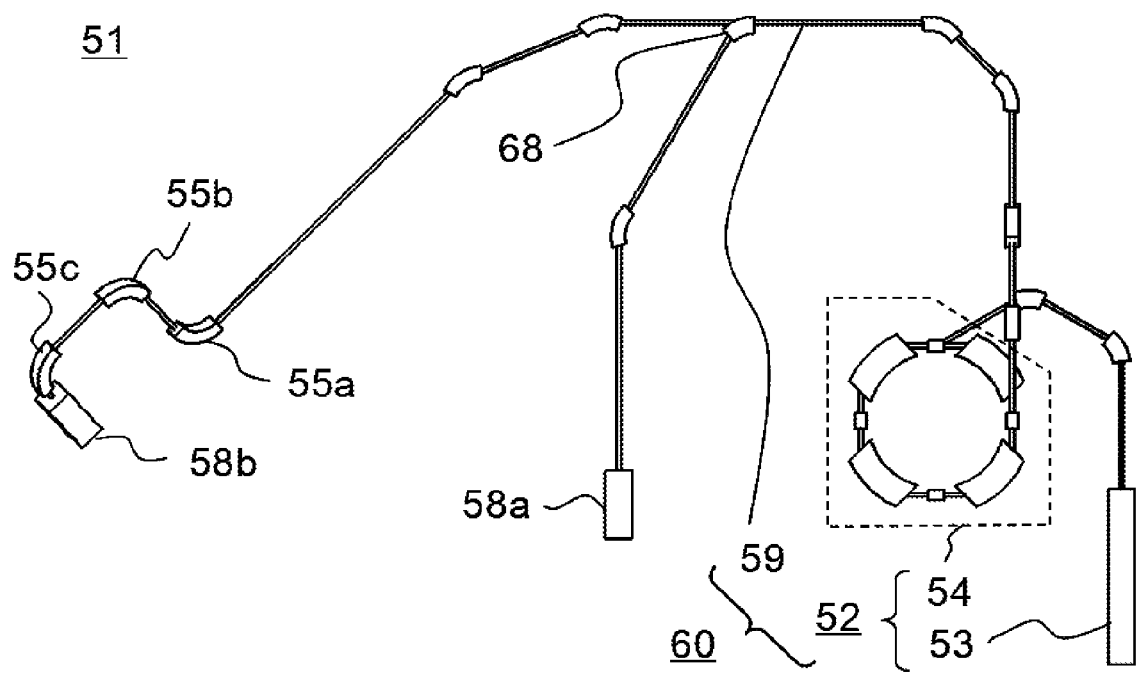
FIG. 1 is a configuration diagram illustrating a particle beam therapy system according to Embodiment 1 of the present invention.
Figure 2:
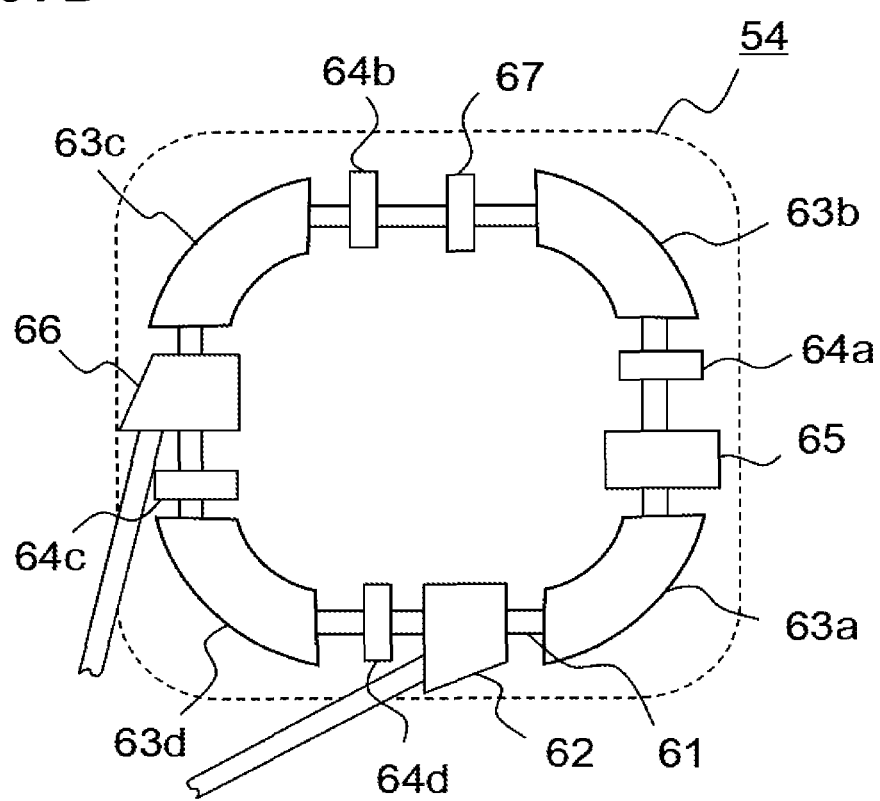
FIG. 2 is a schematic configuration diagram of an accelerator in FIG. 1.
Figure 3:
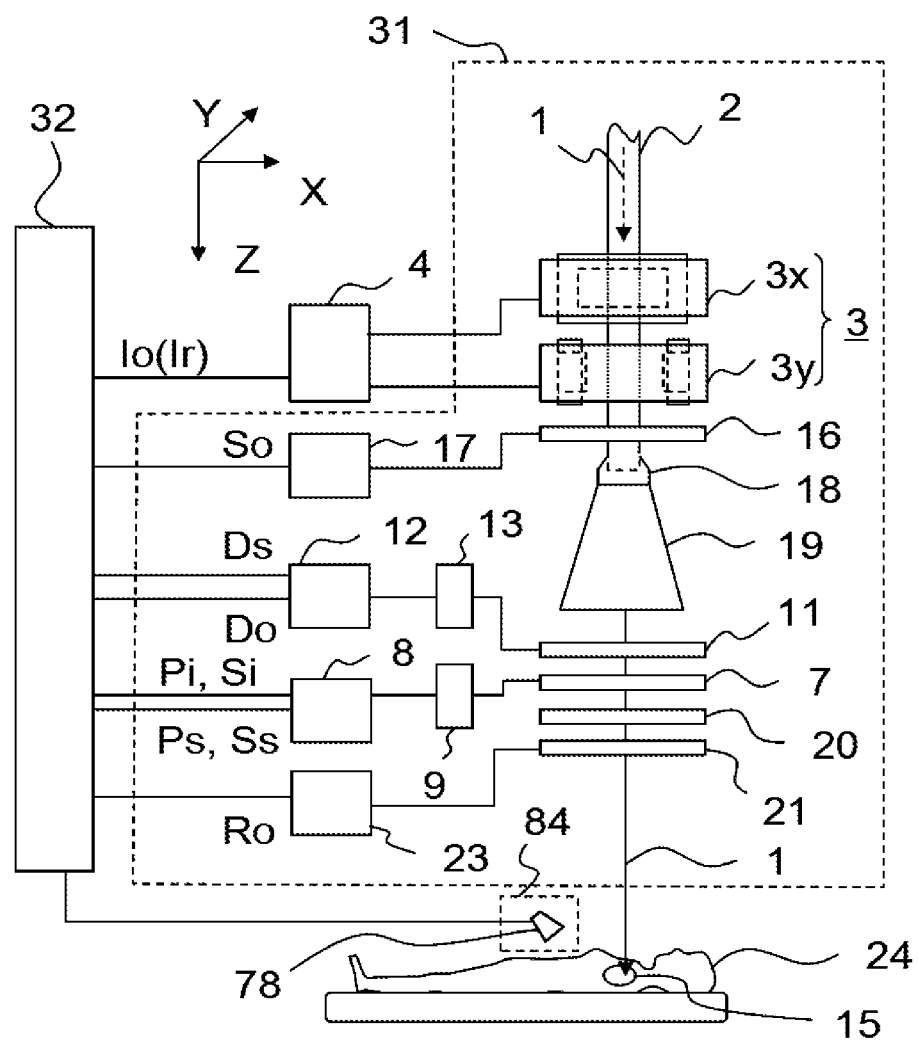
FIG. 3 is a schematic configuration diagram of a particle beam irradiation apparatus in FIG. 1.
Figure 4:
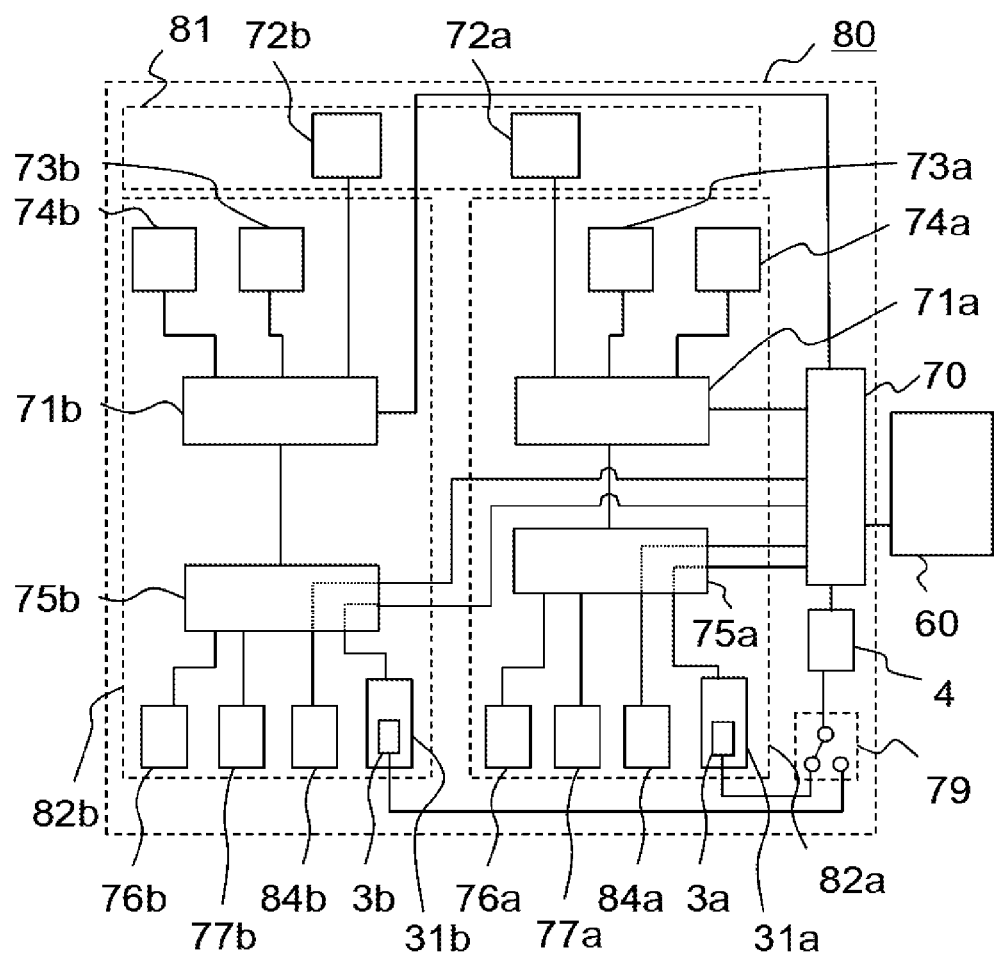
FIG. 4 is a control block diagram illustrating a particle beam therapy system according to Embodiment 1 of the present invention.

The configuration of a particle beam therapy system according to Embodiment 1 of the present invention will be explained below. FIG. 1 is a configuration diagram illustrating a particle beam therapy system according to Embodiment 1 of the present invention. FIG. 2 is a schematic configuration diagram of an accelerator; FIG. 3 is a schematic configuration diagram of a particle beam irradiation apparatus. FIG. 4 is a control block diagram illustrating a particle beam therapy system according to Embodiment 1 of the present invention.

At first, the outline of the configuration of a particle beam therapy system will be schematically explained with reference to FIG. 1. A particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a circular accelerator (simply referred to as an accelerator, hereinafter) 54, which is a synchrotron. The particle beam irradiation apparatus 58b is provided in a rotating gantry (unillustrated). The particle beam irradiation apparatus 58a is provided in a treatment room where no rotating gantry is installed. The function of the beam transport system 59 is to achieve communication between the accelerator 54 and the particle beam irradiation apparatuses 58a and 58b. Part of the beam transport system 59 is provided in the rotating gantry (unillustrated), and that part includes a plurality of deflection electromagnets 55a, 55b, and 55c. The beam generation apparatus 52, the beam transport system 59, and the particle beam irradiation apparatuses 58a and 58b are controlled by a control system in a collaborative manner.

A charged particle beam 1, which is a particle beam such as a proton beam generated in ion source or a carbon beam (heavy particle beam), is accelerated by the prestage accelerator 53 and enters the accelerator 54. The particle beam 1 is accelerated to obtain predetermined energy. The charged particle beam 1 is accelerated by the accelerator 54 in a high-frequency electric field up to 70% to 80% of the light velocity, as it is being bent by means of the magnets. The charged particle beam 1 launched from the accelerator 54 is transported to the particle beam irradiation apparatuses 58a and 58b by way of the beam transport system 59. In the beam transport system 59, the charged particle beam 1 that has received sufficient energy is guided through a path created with a vacuum duct to the particle beam irradiation apparatuses 58a and 58b in respective designated treatment rooms, while its orbit is changed by the electromagnets, as may be necessary. The particle beam irradiation apparatuses 58a and 58b each form an irradiation field in accordance with the size and the depth of the diseased site of a patient 24 as an irradiation subject 15, and each irradiate the charged particle beam 1 onto the irradiation subject 15 (refer to FIG. 3).

Meanwhile, in the foregoing sentence, the phrase "respective designated treatment rooms" has been described; in general, in view of the therapy efficiency, a particle beam therapy system has a plurality of treatment rooms. That is to say, it is required to provide particle beam irradiation apparatuses 58 as many as the number of treatment rooms. In many cases, a large-size complex system configured with a plurality of subsystems, in general, includes a sub-controller that is dedicated to control of each subsystem and a main controller that conducts and controls the whole system. The particle beam therapy system 51 according to Embodiment 1 of the present invention will be explained based also on a case where this configuration with a main controller and a sub-controller is adopted. For the sake of simplicity, the beam generation apparatus 52 and the beam transport system 59 will be herein referred to as an accelerator system 60. The system consisting of the particle beam irradiation apparatus 58 and the rotating gantry will be referred to as an "irradiation system". FIG. 1 illustrates a case where there exist two treatment rooms, i.e., a horizontal irradiation room and a gantry irradiation room. The foregoing controller that controls the accelerator system and the irradiation system in a collaborative manner is a control system of the particle beam therapy system.

<Accelerator>

The accelerator 54 will be explained with reference to FIG. 2. The accelerator 54 is provided with a vacuum duct 61 that serves as an orbit path through which the charged particle beam 1 circulates; an injector 62 for injecting the charged particle beam 1, supplied from a prestage accelerator 53, into the vacuum duct 61; deflection electromagnets 63a, 63b, 63c, and 63d for deflecting the orbits of charged particles so that the charged particles form the charged particle beam 1 that circulates along a circulation orbit in the vacuum duct 61; convergence electromagnets 64a, 64b, 64c, and 64d for converging the charged particle beam 1 formed on the circulation orbit not to diverge; a high-frequency wave acceleration cavity 65 that applies a high-frequency voltage, synchronized with circulating charged particles, to the circulating charged particles so as to accelerate the charged particles; an emission apparatus 66 for extracting from the accelerator 54 the charged particle beam 1 accelerated in the accelerator 54 and emitting the extracted charged particle beam into the beam transport system 59; and a six-pole electromagnet 67 that excites resonance in the circulation orbit of the charged particle beam 1 in order to make the emission apparatus 66 emit the charged particle beam 1.

There are provided unillustrated apparatuses for controlling the respective units; for example, in the deflection electromagnets 63a, 63b, 63c, and 63d, there are provided deflection electromagnet control apparatuses that control the excitation currents for the deflection electromagnets 63a, 63b, 63c, and 63d, respectively, and in the high-frequency wave acceleration cavity 65, there are provided a high-frequency wave source for supplying a high-frequency voltage to the high-frequency wave acceleration cavity 65 and a high-frequency wave control apparatus for controlling the high-frequency wave source; in the control system, there is provided an accelerator control apparatus that controls the whole accelerator by controlling other components such as the deflection electromagnet control apparatus, the high-frequency wave control apparatus, and the convergence electromagnet 64a, 64b, 64c, and 64d. However, in the technical idea of the present invention, the control of the accelerator itself is not limited; therefore, the accelerator is not limited to the one having the foregoing configuration, and it goes without saying that various modifications are allowed, as long as the variants can stably emit the charged particle beam 1 into the beam transport system 59.

<Beam Transport System>

The charged particle beam 1 accelerated by the accelerator is emitted to the beam transport system 59, which is referred to as an HEBT (High Energy Beam Transport) system. The beam transport system 59 is provided with a vacuum duct that serves as an orbit path of the charged particle beam 1; a switching electromagnet 68, which is a switching device for switching the orbits of the charged particle beam 1; and a deflection electromagnet that deflects a beam at a predetermined angle. The charged particle beam 1 that has been sufficiently energized by the accelerator 54 and travels through the transport path formed of the vacuum duct is led to the irradiation apparatus provided in a designated treatment room; the orbit of the charged particle beam 1 is changed by the switching electromagnet 68, as may be necessary.

<Irradiation System>

The irradiation system includes the particle beam irradiation apparatus 58 that forms the charged particle beam 1 supplied from the beam transport system 59 into an irradiation field conforming to the size or the depth of a diseased site of a patient as the irradiation subject 15 and that irradiates the charged particle beam 1 onto the diseased site. In general, in the particle beam therapy system 51, as irradiation field forming methods, the scatterer method, the Wobbler method, and the scanning method have been proposed. The irradiation systems (particle beam irradiation apparatuses) have different configurations, depending on the irradiation methods thereof. The present invention is to be applied to a particle beam therapy system (referred to also as a "scanning-type particle beam therapy system") utilizing the scanning method typified by spot scanning or raster scanning. When being a scanning-type particle beam therapy system, the particle beam irradiation apparatus 58 is provided with a pair of scanning electromagnets for scanning the pencil-shaped charged particle beam 1 in accordance with the shape of the irradiation subject 15 and a position monitor 7 for measuring an irradiation position and the like. The detailed configuration of the particle beam irradiation apparatus 58 will be described later.

<Control System>

The control system will be explained with reference to FIG. 4, which illustrates the functional block. Meanwhile, in general, as the controller of the particle beam therapy system 51, a workstation or a computer is utilized. Accordingly, in many cases, the controller is referred to as a "computer". For example, the main controller 70 in FIG. 4 is, in fact, a function of a computer, which is, in many cases, referred to as an irradiation system common computer; however, the main controller 70 is dealt with as a controller having a specific function. Each of the sub-controllers 71a and 71b is a function of a computer, which is, in many cases, referred to as an apparatus control computer; however, each of the sub-controllers 71a and 71b is dealt with as a controller having a specific function. The sub-controllers 71a and 71b perform control of the whole subsystems, which consists of a part of apparatuses in the treatment room, such as a treatment table for laying a patient 24 and an X-ray image-capturing device for radiographing the position of a diseased site (irradiation subject 15).

An irradiation system 80 is configured with the main controller 70, apparatuses provided in an irradiation operation room 81, apparatuses provided in a treatment room 82a, and apparatuses provided in a treatment room 82b. In the treatment room 82a, there is arranged an irradiation apparatus unit 31a of the particle beam irradiation apparatus 58a. In the treatment room 82b, there is arranged an irradiation apparatus unit 31b of the particle beam irradiation apparatus 58b.

The "consoles" 72a, 72b, 73a, 73b, 74a, and 74b connected with the sub-controllers 71a and 71b are each a keyboard, a display, or the like or a terminal such as a controller box; in other words, they are each a man-machine interface. The consoles 72a and 72b are provided in the irradiation operation room 81; the consoles 73a and 74a are provided in the treatment room A (82*a*); the consoles 73*b* and 74*b* are provided in the treatment room B (82*b*). Control boards 75*a* and 75*b* are connected with the bottom parts of the sub-controllers 71*a* and 71*b*, respectively. Each of the control boards 75*a* and 75*b* includes, specifically, a driver, an amplifier, a sequencer, and the like for various kinds of apparatuses 76*a*, 76*b*, 77*a*, and 77*b*, which are control subjects. The control board 75*a* allows communication of signals between the main controller 70 and an interlock information inputting device 84*a* and between the main controller 70 and the irradiation apparatus unit 31*a*; the control board 75*b* allows communication of signals between the main controller 70 and an interlock information inputting device 84*b* and between the main controller 70 and the irradiation apparatus unit 31*b*. The apparatuses 76*a* and 77*a*, the interlock information inputting device 84*a*, and the irradiation apparatus unit 31*a* are connected with the bottom part of the sub-controllers 71*a* by way of the control board 75*a*; the apparatuses 76*b* and 77*b*, the interlock information inputting device 84*b*, and the irradiation apparatus unit 31*b* are connected with the bottom part of the sub-controllers 71*b* by way of the control board 75*b*. Each of the apparatuses 76*a*, 76*b*, 77*a*, and 77*b* is, specifically, a motor for moving the respective axles of a treatment table, a motor for driving an X-ray image-capturing device in the irradiation apparatus, or the like. A scanning electromagnet power source 4 supplies respective energization currents to scanning electromagnets 3*a* and 3*b* provided in the irradiation apparatus units 31*a* and 31*b*, respectively, by way of a switching circuit 79.

The motor for the treatment table and the motor for the X-ray image-capturing device are not moved when a beam is being irradiated. That is to say, it is not required to implement control in synchronization with the electromagnet for the accelerator and the like controlled by the accelerator system 60. In order to exchange information about their conditions, the main controller 70 and the sub-controller 71*a* or 71*b* communicate with each other, for example, by use of a Ready signal that indicates in which treatment room the irradiation apparatus unit 31*a* or 31*b* has completed its positioning and is ready to irradiate a beam, and a signal that indicates in which treatment room the irradiation apparatus unit 31*a* or 31*b* has irradiated a beam and completed its irradiation, and the like. Briefly speaking, it is regarded as carrying out events sequentially.

Here, the functions of the irradiation system common computer (main controller 70) and the apparatus control computers (sub-controllers 71*a* and 71*b*) will be explained. As described above, in the treatment rooms 82*a* and 82*b*, there are provided the irradiation apparatus units 31*a* and 31*b* of the particle beam irradiation apparatuses 58*a* and 58*b*, respectively. Additionally, as described above, in the case of a scanning-type particle beam therapy system, in each of the irradiation apparatus units 31*a* and 31*b*, there are provided a pair of scanning electromagnets 3, the position monitor 7 for measuring an irradiation position, and the like. In this regard, however, as illustrated in FIG. 4, control of the scanning electromagnets 3 and processing of signals from the position monitor 7 are performed not by the apparatus control computer but by the irradiation system common computer (an irradiation management apparatus, described later).

The foregoing fact is based on two reasons. The first reason is requirement for control in synchronization with the accelerator system; the second reason is instantaneousness (requirement for reducing wasteful time as much as possible). In order to realize irradiation as per a treatment plan, it is required to control the accelerator system 60 and the irradiation system 80 in such a way that they are synchronized with each other. It is true that the sub-controllers 71*a* and 71*b* and the main controller 70 can perform processing at the same time and in a parallel manner, by use of a synchronization signal or the like. However, the more apparatuses to be passed through there are, the more wasteful time occurs and hence control performance is deteriorated. Accordingly, in the particle beam therapy system 51 according to the present invention, the accelerator system 60, the scanning electromagnet 3, and the like, which need to be controlled in real time during irradiation of a beam, are controlled by the irradiation system common computer (the irradiation management apparatus), which is the main controller 70; in contrast, the treatment table, the X-ray image-capturing device, and the like, which do not need to be driven during irradiation of a beam, are controlled by the apparatus control computers, which are the sub-controllers 71*a* and 71*b*.

This is because intensive management by a single main controller 70 can reduce wasteful time as much as possible, thereby realizing high-accuracy beam irradiation without deteriorating the control performance. For the purpose of ensuring the instantaneousness, as well, it is desirable that signal processing for the interlock information inputting devices 84*a* and 84*b* and the like, which function as the interlock (emergency-stop processing), and the like are performed by the irradiation system common computer (the irradiation management apparatus), which is the main controller 70. The irradiation system common computer is provided with a so-called "contest for accelerator" function in which it is managed which treatment room occupies the charged particle beam 1.

Next, the particle beam irradiation apparatus 58 will be explained with reference to FIG. 3. The particle beam irradiation apparatus 58 is provided with the irradiation apparatus unit 31, the scanning electromagnet power source 4, the interlock information inputting device 84, and an irradiation management apparatus 32 that performs control of the irradiation apparatus unit 31 and the interlock information inputting device 84, collection of data, and the like. The interlock information inputting device 84 is provided with a patient sensor 78, described later. The irradiation apparatus unit 31 is provided with a beam transport duct 2 for transporting the charged particle beam 1 injected by the beam transport system 59; scanning electromagnets 3*x* and 3*y* that scan the charged particle beam 1 in the X direction and the Y direction, respectively, which are directions perpendicular to the charged particle beam 1; a position monitor 7; a preamplifier 9 that amplifies a signal from the position monitor 7; a position monitor unit 8; a dose monitor 11; a preamplifier 13 that amplifies a signal from the dose monitor 11; a dose monitor unit 12; a beam enlargement apparatus 16; a beam enlargement control apparatus 17; a bellows 18; a vacuum duct 19; a ripple filter 20; a range shifter 21; and a range shifter unit 23. As illustrated in FIG. 3, the incident direction of the charged particle beam 1 is the Z direction.

The scanning electromagnet 3*x* is an X-direction scanning electromagnet that scans the charged particle beam 1 in the X direction; the scanning electromagnet 3*y* is a Y-direction scanning electromagnet that scans the charged particle beam 1 in the Y direction. The position monitor 7 detects the size of the charged particle beam 1, which has been deflected by the scanning electromagnets 3*x* and 3*y*, and the passing position (the gravity center position) through which the charged particle beam 1 passes. The preamplifier 9 amplifies analogue data on the passing position and the beam size detected by the position monitor 7. Here, the beam size denotes an area, in the XY plane perpendicular to the Z direction, through which the charged particle beam 1 passes. The position monitor unit 8 receives the passing position and the beam size detected by the position monitor 7, through the preamplifier 9; then, the position monitor unit 8 converts the passing position and the beam size into digital data so as to create measured position coordinates Ps and a measured beam size Ss.

The dose monitor 11 detects the dose of the charged particle beam 1. The preamplifier 13 amplifies analogue data on the dose detected by the dose monitor 11. The dose monitor unit 12 receives the dose detected by the dose monitor 11, through the preamplifier 13; then, the dose monitor unit 12 converts the dose into digital data so as to create a measured dose Ds.

The beam enlargement apparatus 16 enlarges the beam size of the charged particle beam 1, as may be necessary. The vacuum duct 19 ensures a vacuum region through which the charged particle beam 1 passes. The bellows 18 connects the beam transport duct 2 with the vacuum duct 19 in an expandable/contractible manner and extends the vacuum region toward the irradiation subject 15. The ripple filter 20 is also referred to as a ridge filter and formed in a convex shape. The ripple filter 20 causes an energy loss to the charged particle beam 1, which is a monochromatic beam having approximately single energy and transported from the accelerator 54, so that the energy has a range.

The depth-direction (Z direction) position coordinates of the irradiation subject 15 is controlled by varying the energy of the charged particle beam 1 through change in the acceleration energy of the accelerator 54 and by varying the energy of the charged particle beam 1 through the range shifter 21. The range shifter 21 adjusts the range of the charged particle beam 1 little by little. Considerable change of the range of the charged particle beam 1 is performed by changing the acceleration energy of the accelerator 54, and slight change of the range of the charged particle beam 1 is performed by changing the setting of the range shifter 21.

The irradiation management apparatus 32 reads the treatment plan data pieces F0 generated by the treatment planning apparatus; then, in order to control the irradiation dose, the irradiation management apparatus 32 creates setting data Fi by rearranging the treatment plan data pieces in order of irradiation onto irradiation spots, which are divided irradiation units. In other words, the setting data Fi is sequentialized treatment plan data (sequential data, described later). Based on the setting data Fi, the irradiation management apparatus 32 outputs the setting data pieces Fo, which are respective commands to the apparatuses.

The elements of the setting data Fi are desired irradiation position coordinates Pi, a desired dose Di, a desired beam size Si, a desired accelerator setting Bi, and a range shifter insertion amount Ri; respective elements of the setting data Fi are data items obtained by sequentializing a desired irradiation position coordinates Pi0, a desired dose Di0, a desired beam size Si0, a desired accelerator setting Bi0, and a range shifter insertion amount Ri0, which are the elements of the treatment plan data F0. The setting data Fo includes an accelerator setting command Bo, a range shifter command Ro, a command current Io (an uncorrected command current), a command current Ir (a command current obtained by correcting the command current Io), a beam size command So, and a desired dose Do.

The irradiation management apparatus 32 receives irradiation records such as the measured position coordinates Ps, the measured dose Ds, and the measured beam size Ss in preliminary irradiation performed when the patient 24 does not exist, and evaluates the irradiation records. The irradiation management apparatus 32 creates the command current Ir by correcting the command current Io, based on the measured position coordinates Ps, and transmits the command current Io or the command current Ir to the scanning electromagnet power source 4. The irradiation management apparatus 32 receives irradiation records, such as the measured position coordinates Ps, the measured dose Ds, and the measured beam size Ss in actual irradiation where irradiation onto the patient 24 is actually performed, and stores the irradiation records in the actual irradiation in the patient file server.

The irradiation management apparatus 32 outputs a trigger signal, a count start signal, a beam supply command, and a beam stop command, and controls the irradiation spot and the irradiation dose at the irradiation subject 15. The irradiation spots are layers divided in the Z direction; each irradiation spot is divided into a slice, which corresponds to the kinetic energy of the charged particle beam 1, and the XY direction at each slice. In this embodiment, there will be explained an irradiation method in which the charged particle beam 1 is stopped when slices are changed, and the charged particle beam 1 is continuously irradiated when irradiation is performed within a single and the same slice. The irradiation management apparatus 32 scans the charged particle beam 1 onto respective slices, of the irradiation subject 15, that are layers corresponding to kinetic energy levels. The irradiation management apparatus 32 changes setting of each apparatus for each irradiation spot in response to the trigger signal, and starts to measure the irradiation dose of an irradiation spot in response to the count start signal; when the measured dose Ds reaches the desired dose Do, the irradiation management apparatus 32 performs control for the next irradiation spot; when respective irradiations onto irradiation divisions (slices) obtained by dividing the irradiation subject 15 are completed, the irradiation management apparatus 32 outputs the beam stop command to the accelerator system 60 so as to stop the charged particle beam 1. Next, the irradiation management apparatus 32 outputs the trigger signal and sequentially changes the corrected command current Ir, the beam size command So, the accelerator setting command Bo, and the range shifter command Ro; then, the irradiation management apparatus 32 performs irradiation of the charged particle beam 1 until irradiation onto all the slices of the irradiation subject 15 is completed.

The scanning electromagnet power source 4 changes the setting currents for the scanning electromagnets 3x and 3y, based on the command current Io (Ir), which is outputted from the irradiation management apparatus 32 and is a control input to the scanning electromagnet 3. The beam enlargement control apparatus 17 outputs to the beam enlargement apparatus 16 the beam size command So for setting the beam size at the position monitor 7. The range shifter unit 23 outputs to the range shifter 21 the range shifter command Ro for changing the energy of the charged particle beam 1.

The patient sensor 78 detects the motion of the patient 24 and outputs a patient signal on which the motion of the patient 24 is reflected. The patient sensor 78 is to stop irradiation when the motion of the patient exceeds a predetermined range, i.e., to perform emergency-stop processing for the particle beam therapy system. As the patient sensor 78, the following devices may be utilized. Specifically, there are conceivable a method of detecting the flow of expired air by means of a flow sensor, a method of measuring the temperature change, due to inspiration, in the vicinity of nasal cavities through image processing by a thermistor or an infra-red camera, a method of detecting the abdominal movement of a patient by means of a position sensitive detector (position sensor) that senses a laser-beam source mounted on the abdomen, and a method of converting the abdominal movement of a patient into a signal by means of a laser displacement gauge. Additionally, the patient sensor 78 may be utilized also as the respiratory sensor that is utilized for respiration-synchronized irradiation of the particle beam therapy system 51. This is because both the respiratory sensor and the patient sensor are utilized for the purpose of detecting the motion of the patient 24.

Next, the technology disclosed in Patent Document 1, which is a basis of the present invention, will briefly be explained. The invention disclosed in Patent Document 1 has been implemented for the particle beam therapy system 51 that irradiates the charged particle beam 1, accelerated by the accelerator 54 and scanned by the scanning electromagnet 3, onto the irradiation subject 15; the particle beam therapy system has the following characteristics:

(A) There is provided the irradiation management apparatus that controls the scanning electromagnet 3, based on the desired irradiation position coordinates Pi of the charged particle beam 1;

(B) There is provided a position monitor 7 that measures the measured position coordinates Ps of the charged particle beam 1; and (C) The irradiation management apparatus 32 is provided with a command value generator that outputs the control input Io (Ir) to the scanning electromagnet 3, based on the desired irradiation position coordinates Pi and the correction data Ia generated on the basis of the measured position coordinates Ps, measured by the position monitor 7 in the preliminary irradiation in which the excitation pattern of the scanning electromagnet 3 is the same as that of the actual irradiation plan, and the desired irradiation position coordinates Pi.

Figure 5:
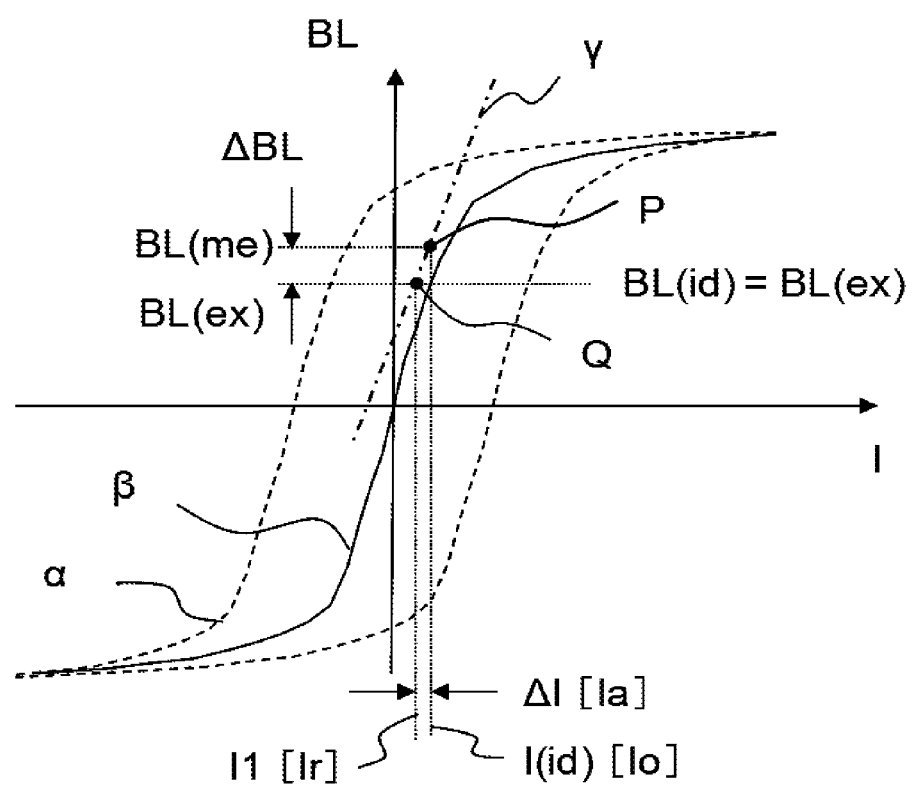
FIG. 5 is a graph for explaining a method of correcting a command current.

The method of creating the current correction data Ia will be explained. FIG. 5 is a graph for explaining a method of correcting a command current. There is measured the BL product vs. the current I, which is outputted to the scanning electromagnet 3 in response to the command current Io applied to the scanning electromagnet power source 4. The BL product is multiplication product of the intensity B of the magnetic field and the effective length L of the magnetic pole of the scanning electromagnet 3. There is drawn a maximum hysteresis curve α that passed through the saturated magnetic flux density. By averaging the one portion of the maximum hysteresis curve α, which is drawn in such a way that the current increase, and the other portion of the maximum hysteresis curve α, which is drawn in such a way that the current decreases, the center line β of the hysteresis loop is obtained.

The current value I(id) set through the command current Io is determined by the desired irradiation position coordinates Pi, at which irradiation is performed, the center line β of the hysteresis loop, the energy of the charged particle beam 1, and the distance between the position at which the scanning electromagnet 3 is disposed and the irradiation position. While considering the Lorentz force exerted on the charged particle beam 1, the value of the BL product can be obtained from the position coordinates of the charged particle beam 1. The command current Io is a command value that corresponds to the current I(id) at the intersection point P' (not represented) of the value BL(id) of the ideal BL product calculated from the desired irradiation position coordinates Pi with the center line β of the hysteresis loop. BL(id) is the expected value BL(ex) of the value of the BL product to be measured.

A value BL(me) of the BL product is calculated from the measured position coordinates Ps. The point P in FIG. 5 is the actually measured value. There will be considered a case where the value BL(me) of the measured BL product is displaced by ΔBL from the expected value BL(ex). In order to correct the current, the displacement by ΔBL is made by use of a straight line having a gradient K, which is a tangential line at the intersection point P' at which the command current Io is obtained. In order to make a correction, there is obtained the current value I1 at which the BL product becomes BL(ex). After the current value I1 is obtained, there can be generated the command current Ir for setting the current value to the current value I1 corresponding to BL(id). In such a way as described above, the displacement of the charged particle beam 1 due to the hysteresis of the scanning electromagnet 3 can be made to fall within a tolerance range.

The straight line (dashed line) γ is a line having the gradient K that is the same as the gradient of the tangential line, at the current value I(id), of the center line β. The gradient K can be expressed by the equation (1), and the corrected current value I1 can be expressed by the equation (2).

$$K = \frac{dBL}{dI}(id) \tag{1}$$

$$I1 = I(id) - \frac{\Delta BL}{K} \tag{2}$$

where ΔBL=BL(me)−BL(ex). The correction current value ΔI to be set through the current correction data Ia is ΔBL/K.

Next, there will be considered a case where emergency-stop processing for the particle beam therapy system 51 is performed. As described above, the emergency-stop processing is processing of interrupting irradiation when a contingency occurs. The situation where the emergency-stop processing should be performed is, for example, a case where the measured position coordinates Ps or the measured beam size Ss, of the charged particle beam 1, detected by the position monitor 7 exceeds an allowable value, or a case where there occurs such a contingency as the patient 24 becomes ill, or the like. FIG. 3 illustrates a case where the particle beam irradiation apparatus 58 according to Embodiment 1 is provided with the patient sensor 78 that detects the motion of a patient; however, there are provided therein a patient call button (unillustrated) for the patient 24 to inform that the patient 24 himself or herself has become ill and an irradiation stop button (unillustrated) that enables a doctor or an engineer or the like to stop irradiation in the event of an emergency. Each of the patient sensor 78, the patient call button, the irradiation stop button, and the position monitor 7 works as the interlock information inputting device 84 that generates an interlock signal that activates the interlock function for stopping beam irradiation in the event of an contingency so as to ensure the safety. The interlock information inputting device 84 includes a signal generator that generates the interlock signal from a signal outputted by the patient sensor 78, the patient call button, the irradiation stop button, or the position monitor 7.

As described above, in the interlock processing (emergency-stop processing), instantaneousness is required; thus, it is desirable that this signal processing is performed by the irradiation system common computer (irradiation management apparatus 32), which is the main controller 70. The irradiation management apparatus 32, which is the main controller 70, according to Embodiment 1 of the present invention has the following characteristics.

The irradiation management apparatus 32 determines that irradiation should be stopped, when the motion of the patient 24 exceeds a predetermined range, from a signal (the patient signal) detected by the patient sensor 78. The irradiation management apparatus 32 determines that irradiation should be stopped, when the measured position coordinates Ps or the measured beam size Ss of the charged particle beam 1, detected by the position monitor 7, exceeds a predetermined range (an allowable value) (corresponding to a case where the quality of the charged particle beam 1 is deteriorated). The irradiation management apparatus 32 determines that irradiation should be stopped also in the event of an emergency where by operating the patient call button, the patient 24 informs that he has become ill, or an emergency where by operating the irradiation stop button, a doctor or an engineer or the like expresses his or her will to stop irradiation. The irradiation management apparatus 32, which is the main controller 70, controls also the accelerator system 60 (the accelerator 54, the beam transport system 59); therefore, when determining that irradiation should be stopped, the irradiation management apparatus 32 can stop the irradiation of the charged particle beam 1, by controlling the accelerator system 60. The predetermined range for the motion of the patient 24 detected by the patient sensor 78 is a range obtained by adding a margin to the detection value corresponding to the moving range of the patient 24 at a time when the patient 24 normally respires. There will be described later the method in which the motion of the patient 24 is detected and then it is determined whether or not the motion has exceeded the predetermined range.

The irradiation management apparatus 32 according to Embodiment 1 is further provided with the following characteristics. As described above, the irradiation management apparatus 32 includes a command value generator that outputs correction data Ia generated based on preliminary irradiation and a control input for the scanning electromagnet 3. That is to say, the irradiation management apparatus 32 includes a control input, as sequential data, preliminarily corrected by the command value generator. The sequential data denotes such data as is implemented step by step (every discrete processing that is implemented in a predetermined time). Because the desired irradiation position coordinates Pi is given as sequential data, there is required, also as sequential data, the control input, for the scanning electromagnet 3, that corresponds to the desired irradiation position coordinates Pi. Base on the interlock signal generated by the interlock information inputting device, the irradiation management apparatus 32 performs the foregoing determination on irradiation stop; when the irradiation is stopped, the irradiation management apparatus 32 stores the step (stop step) corresponding to that desired irradiation position coordinates Pi (i.e., stop position coordinates) in a stop step storage memory, which is incorporated therein. For example, there is stored the number "n" of a step in which there is outputted a control input corresponding to the desired irradiation position coordinates Pi in a given slice (stop step storage procedure). The stop step storage memory may be provided not only in the irradiation management apparatus 32 but also outside the irradiation management apparatus 32.

The irradiation management apparatus 32 according to Embodiment 1 of the present invention is further provided with the following characteristics. In particle beam therapy, a single therapy time is approximately 30 minutes; out of the 30 minutes, several minutes are for irradiation. It cannot necessarily be said that during the particle beam therapy, there occurs no contingency such as the patient 24 becoming ill, the patient 24 having a coughing fit, or the quality of the charged particle beam 1 being deteriorated. The case where the measured position coordinates Ps or the measured beam size Ss of the charged particle beam 1, detected by the position monitor 7, exceeds a predetermined range (an allowable value) corresponds to a case where the quality of the charged particle beam 1 is deteriorated. In this case, irradiation is stopped through sensing by a sensor or by operating a button or the like so that the therapy is interrupted. In the case where the foregoing contingency is cancelled and irradiation is resumed, the irradiation management apparatus 32 controls the scanning electromagnet 3 with a beam unirradiated, for example, from the initial step for a given slice (idle operation procedure). Control of the scanning electromagnet 3 with a beam unirradiated will be referred to herein as "idle operation". The step where the idle operation is started will be referred to as a start step.

This is for the following reason. When irradiation is resumed simply from an irradiation position at which the irradiation has been interrupted, control of the scanning electromagnet 3 is performed halfway through the excitation pattern; however, when the scanning electromagnet 3 is controlled from the initial step for a given slice, the control can be performed with the same excitation pattern as the preliminary irradiation has been performed. It goes without saying that when a beam is irradiated at this timing, double irradiation is caused; thus, it is significant to perform the idle operation. Accordingly, correction based on the preliminary irradiation becomes effective, and high-accuracy beam irradiation can be performed at the same level as when there exists no interruption.

In view of the reproducibility, it is desirable to perform the idle operation from the initial step for a given slice; however, it is empirically known that even when the idle operation is performed from a step that is predetermined steps (predetermined spots) prior to the step corresponding to the stop position, a considerable effect can be obtained. Thus, in Embodiment 1, as the start step, there is selected the initial step for a given slice, or is selected the step that is prior to the step corresponding to the stop position by predetermined steps which are preliminarily set. That is to say, the operator such as a doctor or an engineer can make selection between idle operation to be performed from the initial step for a given slice and idle operation to be performed from a step that is prior to the step corresponding to the stop position by predetermined steps which are preliminarily set.

Here, there will be explained the method of making decision on how many the predetermined steps should be. The effective number of steps for the idle operation depends mainly on the scale or the performance of the scanning electromagnet 3. Thus, it is desirable that an interrupted situation is actually and intentionally reproduced, experiments are carried out with a different number of steps, and after the confirming the effect, the number of steps is decided. In some cases, the idle operation is performed from halfway through the immediately previous slice. It is allowed that, as described above, the idle operation is performed from a step that is prior to the initial step for a given slice.

Lastly, it is required that the irradiation management apparatus 32 controls the particle beam irradiation apparatus in such a way that there is irradiated the portion onto which a beam has not been irradiated due to interruption. Therefore, the irradiation management apparatus 32 controls the accelerator system 60 (the accelerator 54, the beam transport system 59) in such a way that after idle operation is carried out up to a step corresponding to the stop position, beam irradiation is started from the resumption step that follows the stop step, so that the remaining steps can be performed (irradiation start procedure). In the case of an irradiation method in which the charged particle beam 1 is stopped when slices are changed and the charged particle beam 1 is continuously irradiated when irradiation is performed within a single and the same slice, sequential time management (step management) enables the irradiation position and the irradiation dose at the irradiation position to be reproduced. That is to say, even in the case where the irradiation dose at an irradiation spot, which is a stop position where irradiation has been interrupted, has not reached the desired dose Do, irradiation is resumed with a halfway irradiation dose, and after the irradiation dose at the irradiation spot reaches the desired dose Do, irradiation can move to the next irradiation spot.

Figure 6:
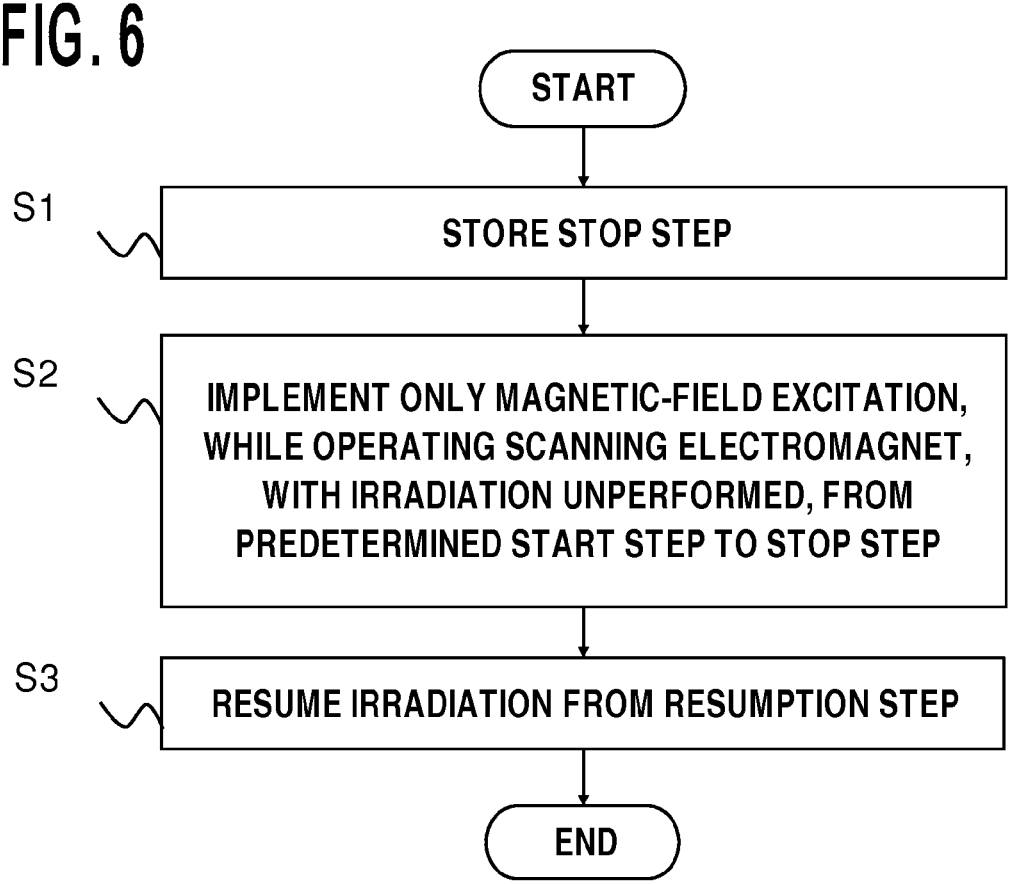
FIG. 6 is a flowchart representing a procedure for stopping and resuming beam irradiation in a particle beam therapy system according to Embodiment 1 of the present invention.

The characteristics of the irradiation management apparatus 32 have been explained; the flow of the emergency-stop processing by the particle beam therapy system 51 will be summarized by use of FIG. 6. FIG. 6 is a flowchart representing a procedure for stopping and resuming beam irradiation in a particle beam therapy system according to Embodiment 1. In the case where during the particle beam therapy, there occurs a contingency such as the patient 24 becoming ill, the patient 24 having a coughing fit, or the quality of the charged particle beam 1 being deteriorated, the irradiation management apparatus 32 performs the foregoing determination on irradiation stop, based on the interlock signal generated by the interlock information inputting device, and stops the irradiation. When the irradiation is stopped, the irradiation management apparatus 32 stores the step corresponding to that desired irradiation position coordinates Pi (i.e., stop position coordinates). For example, there is stored the number "n" of a step in which there is outputted a control input corresponding to the desired irradiation position coordinates Pi in a given slice (the step S1: the stop step storage procedure). In the case where the foregoing contingency is cancelled and irradiation is resumed, the irradiation management apparatus 32 activates the scanning electromagnet power source 4, with a beam unirradiated in the process from a predetermined start step to the stop step, so as to perform only magnetic-field excitation of the scanning electromagnet 3 (the step S2: the idle operation procedure). After the idle operation is carried out up to a step corresponding to the stop position, the irradiation management apparatus 32 controls the accelerator system 60 (the accelerator 54, the beam transport system 59) from the resumption step that follows the stop step so as to resume beam irradiation (the step S3, the irradiation start procedure).

As a result, in the particle beam therapy system 51 according to Embodiment 1, even in the case where a contingency such as a patient becoming ill occurs, irradiation can be interrupted by operating a sensor or a button or the like, and the scanning electromagnet 3 is controlled, with a beam unirradiated, from the initial step for a given slice or from a step that is predetermined steps before (start step); thus, the excitation pattern for the scanning electromagnet 3 is made the same as that at a time when preliminary irradiation is performed, correction based on the preliminary irradiation (i.e., information from the preliminary irradiation) can be made effective, and hence high-accuracy beam irradiation can be realized. Accordingly, even in the case where the emergency-stop processing is performed during therapy, the effect of the hysteresis of the scanning electromagnet 3 can be eliminated and high-accuracy beam irradiation can be resumed from an irradiation position where irradiation has been interrupted.

There will be explained the method in which the motion of the patient 24 is detected and then it is determined whether or not the motion has exceeded a predetermined range. A change caused by normal respiration is measured, as a respiratory signal, through the foregoing patient sensor 78 so that there is preliminarily obtained a reference patient status waveform, which is a temporally-changing waveform of a respiratory signal as a reference (reference respiratory signal). A real patient status waveform, generated from a respiratory signal (real respiratory signal) that is measured by the patient sensor 78 during actual irradiation, is compared with a reference patient status waveform, and it is determined whether or not the difference between the real patient status waveform and the reference patient status waveform has exceeded a predetermined range. As the patient sensor 78 for measuring the reference respiratory signal, there is utilized a patient sensor of a type the same (the same measurement principle) as that of the patient sensor 78 for measuring the respiratory signal during therapy.

Figure 7A:
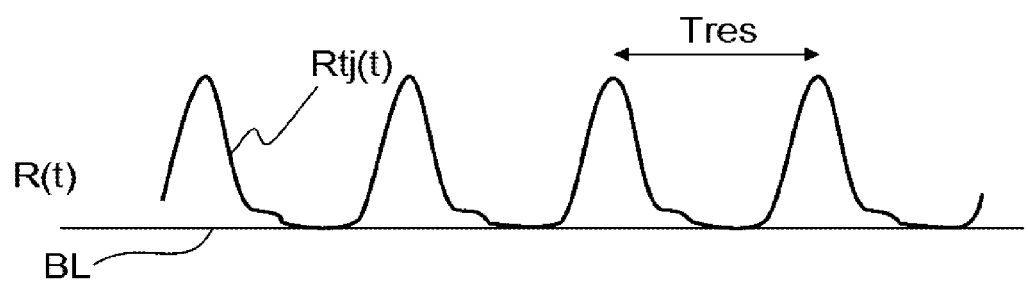
FIG. 7A is a chart representing a reference respiratory signal.

Although not a complete trigonometric function, the reference respiratory signal is a signal of an approximately constant cycle; therefore, there is considered a method in which by converting the reference respiratory signal into a trigonometric function that is closest thereto, the gain (the amplitude of the trigonometric function) and the phase are calculated. Fourier series expansion is applied to the reference respiratory signal $R_{tj}(t)$, for example, as represented in the equation (3); as represented in the equation (4), among the expanded 0th-order term through nth-order term, a pair of coefficients $a_1$ and $b_1$, of the trigonometric function, which correspond to the 1st-order term of the equation (3) are calculated; then, the calculated coefficients $a_1$ and $b_1$ are specified as the describing functions that indicate the state of the respiratory signal. In other words, there are calculated the coefficients $a_1$ and $b_1$ of the cosine function and the sine function that configure the fundamental waveform component that is obtained by removing the constant term and the high-frequency components from the reference respiratory signal. FIG. 7A represents the waveform of a describing function formed of $a_1$ and $b_1$ obtained from the reference respiratory signal $R_{tj}(t)$ and the equation (2).

$$R(t) = \frac{a_0}{2} + \sum_{n=1}^{\infty}(a_n\cos(n\omega_{res}t) + b_n\sin(n\omega_{res}t)) \quad (3)$$

$$\begin{aligned} a_1 &= \frac{1}{\pi}\int_0^{2\pi} R(t)\cos(\omega_{res}t)d\omega_{res}t \\ b_1 &= \frac{1}{\pi}\int_0^{2\pi} R(t)\sin(\omega_{res}t)d\omega_{res}t \end{aligned} \quad (4)$$

As represented in the equations (5) and (6), the gain $G_{res}$ and the phase $\phi_{res}$ can be obtained respectively from $a_1$ and $b_1$ that form the describing function extracted as described above.

$$G_{res} = \sqrt{a_1^2 + b_1^2} \quad (5)$$

$$\phi_{res} = \arctan\frac{b_1}{a_1} \quad (6)$$

Figure 7B:
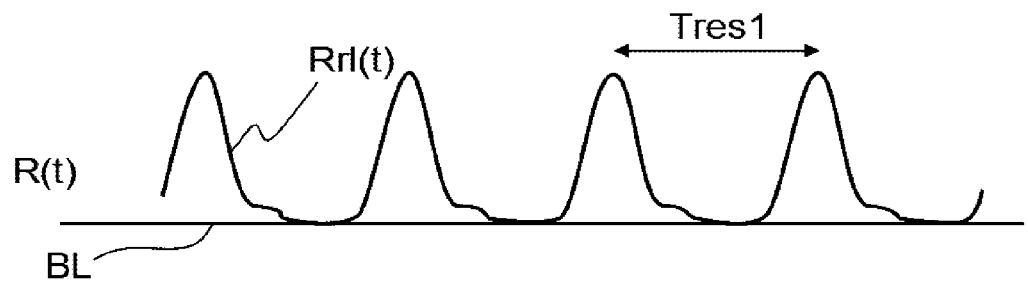
FIG. 7B is a chart representing a real respiratory signal.

FIG. 7A and FIG. 7B are charts representing a reference respiratory signal and a real respiratory signal respectively. FIG. 7A is a chart representing a reference respiratory signal; FIG. 7B is a chart representing a real respiratory signal. The abscissa denotes the time; the ordinate denotes the signal value of the respiratory signal R(t). The cycle of the reference respiratory signal $R_{tj}(t)$ is $T_{res}$; the cycle of the real respiratory signal $R_{rl}(t)$ is $T_{res1}$. Reference character BL in FIG. 7A and FIG. 7B denotes the base line of each of the reference respiratory signal $R_{tj}(t)$ and the real respiratory signal $R_{rl}(t)$. The real respiratory signal $R_{rl}(t)$ is irregular signal. However, for example, when respiratory induction is performed based on the sine wave signal on the basis of the cycle $T_{res}$ of the reference respiratory signal $R_{tj}(t)$ or the reference respiratory signal $R_{tj}(t)$, the real respiratory signal $R_{rl}(t)$ also becomes a cyclic function having a cycle the same as that of the reference respiratory signal $R_{tj}(t)$. By utilizing the respiratory characteristics thereof, as is the case with the reference respiratory signal $R_{tj}(t)$, also with regard to the real respiratory signal $R_{rl}(t)$, there can be calculated a describing function including the pair of coefficients $a_1$ and $b_1$, of the trigonometric functions, that correspond to the 1st-order terms when Fourier series expansion is applied, as represented in the equation (4).

In the case where the motion of the patient 24 is detected and then it is determined whether or not the motion has exceeded a predetermined range, it is only necessary that the cycle $T_{res1}$ of the real respiratory signal $R_{rl}(t)$ approximately coincides with the cycle $T_{res}$ of the reference respiratory signal $R_{tj}(t)$. By setting predetermined ranges for the gain $G_{res}$ and the phase $\phi_{res}$, the ranges of the gain $G_{res}$ and the phase Ores can be adopted as predetermined ranges. For example, when a patient has a coughing fit, the gain and the phase of the real respiratory signal rapidly change; thus, the gain $G_{res}$ and the phase $\phi_{res}$ exceed the predetermined ranges, whereby the motion of the patient caused by the coughing fit can be detected. In addition, when the patient falls into a sleep, the gain of the real respiratory signal gradually becomes small, and the phase of the real respiratory signal gradually loses the correlation with the phase of the reference respiratory signal. Even in this case, by setting appropriate ranges for the gain $G_{res}$ and the phase $\phi_{res}$, there can be detected a fact that the patient has fallen into a sleep or a sign that the patient is going to fall into a sleep.

As described above, in the particle beam therapy system according to Embodiment 1, there are provided the irradiation management apparatus 32 that controls the scanning electromagnet 3, based on the desired irradiation position coordinates Pi of the charged particle beam 1; the position monitor 7 that measures the measured position coordinates Ps of the charged particle beam 1; and the interlock information inputting device 84 that generates an interlock signal for stopping irradiation of the charged particle beam 1, when a contingency occurs. The irradiation management apparatus 32 is provided with a command value generator that outputs the control input Io (Ir) to the scanning electromagnet 3, based on the desired irradiation position coordinates Pi and the correction data Ia generated on the basis of the measured position coordinates Ps, measured by the position monitor 7 in the preliminary irradiation in which the excitation pattern of the scanning electromagnet 3 is the same as that of the actual irradiation plan, and the desired irradiation position coordinates Pi; and a stop step storage memory that stores a stop step corresponding to the desired irradiation position coordinates Pi at which irradiation of the charged particle beam 1 stops, when the interlock signal is generated by the interlock information inputting device 84. When irradiation of the charged particle beam 1 is resumed, the irradiation management apparatus 32 performs idle operation in which the scanning electromagnet 3 is controlled, with the charged particle beam 1 unirradiated, from a start step, which is situated prior to the stop step and is different from the initial step corresponding to the initial desired irradiation position coordinates in actual irradiation, to the stop step, and then the irradiation management apparatus 32 irradiates the charged particle beam 1 from the desired irradiation position coordinates Pi corresponding to the stop step; therefore, in the case where emergency-stop processing is performed during therapy, idle operation is carried out, based on irradiation command data including a control input to the scanning electromagnet 3, from a start step, which is situated prior to the stop step and is different from the initial step, and beam irradiation is started from an irradiation position where the irradiation has been interrupted. As a result, the effect of the hysteresis of the scanning electromagnet 3 is eliminated, so that high-accuracy beam irradiation can be resumed from the irradiation position where the irradiation has been interrupted.

Embodiment 2

In Embodiment 1, there has been described idle operation of the scanning electromagnet 3 at a time when irradiation is resumed after therapy has been interrupted; however, in Embodiment 2, there will be described a method of initializing the scanning electromagnet 3 before the idle operation thereof.

Figure 8:
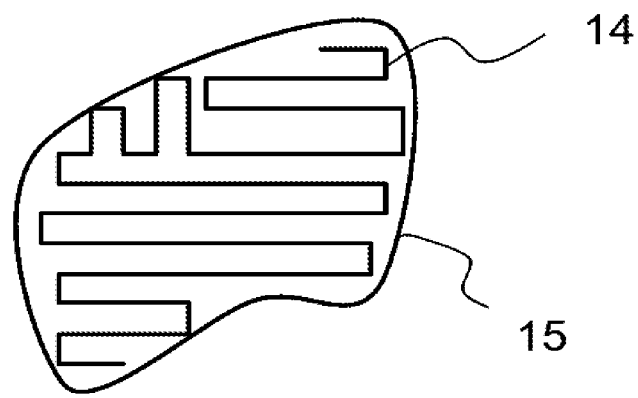
FIG. 8 is a schematic diagram representing a fact that a diseases site is scanned with a beam along a beam path in a particle beam therapy system according to Embodiment 2 of the present invention.

FIG. 8 is a schematic diagram representing a fact that a diseases site is scanned with a beam along a beam path in a particle beam therapy system according to Embodiment 2 of the present invention. The charged particle beam 1 scanned by the scanning electromagnet 3 is irradiated onto each of the layers (slices) of a diseased site such as a cancer, which is the irradiation subject 15, along an irradiation path 14 (referred to also as a beam path). In the scanning-type particle beam therapy system 51, the beam path 14 for each layer is generated by use of a treatment planning apparatus. In the treatment planning apparatus, an optimum treatment plan is generated in such a way that the cancer diseased site is reached through as short path as possible and there exists no unnecessary irradiation onto normal tissues. In the treatment planning apparatus, there is incorporated a computer that performs the optimization; the optimum path is obtained by use of the computer. A doctor, who is a main person (person in charge) for the therapy, eventually determines whether or not the obtained path is optimum. The X-direction scanning electromagnet $3x$ and the Y-direction scanning electromagnet $3y$ are controlled by the irradiation management apparatus 32 in such a way that the charged particle beam 1 is scanned along the generated beam path 14, and the scanning electromagnet power source 4 (referred to also as a pattern power source) supplies a driving current (command current).

Figure 9A:
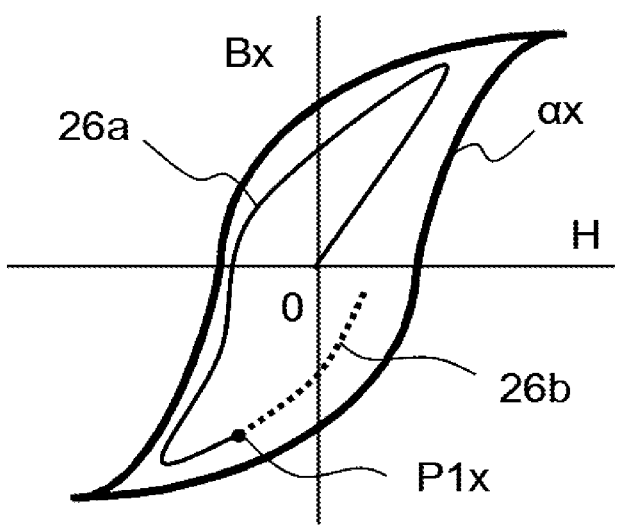
FIG. 9A and FIG. 9B are charts representing the hysteresis characteristics of a scanning electromagnet in a particle beam therapy system according to Embodiment 2 of the present invention.
Figure 9B:
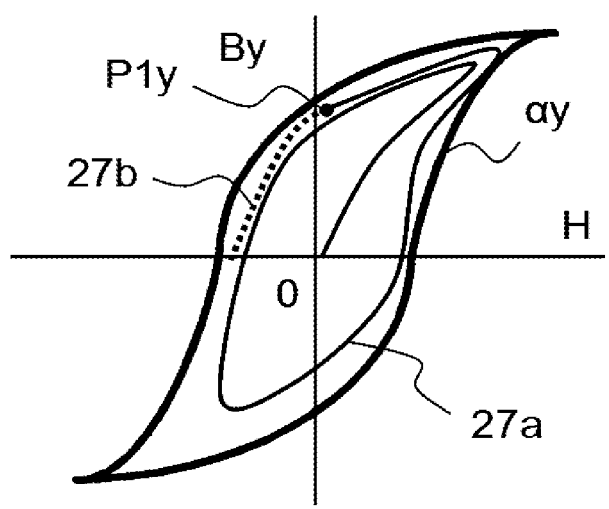

FIG. 9A and FIG. 9B are charts representing the hysteresis characteristics of a scanning electromagnet in a particle beam therapy system according to Embodiment 2. FIG. 9A represents the hysteresis characteristics of the X-direction scanning electromagnet $3x$; FIG. 9B represents the hysteresis characteristics of the Y-direction scanning electromagnet $3y$. As represented in FIG. 9A and FIG. 9B, the magnetic material, which is a material of the scanning electromagnet, has hysteresis characteristics. In FIG. 9A and FIG. 9B, the abscissa denotes the magnetic-field intensity H of a magnetic field generated by an inputted command current; the ordinate denotes the magnetic flux density B. "αx" denotes a maximum hysteresis curve of the X-direction scanning electromagnet $3x$; "αy" denotes a maximum hysteresis curve of the Y-direction scanning electromagnet $3y$. The hysteresis characteristics denote the relationship between the magnetic-field intensity H and the magnetic flux density B in which even when the magnetic-field intensity H is determined, the magnetic flux density B is not uniquely determined simply based on the magnetic-field intensity H, as showed in FIG. 9A and FIG. 9B. In order to realize the beam path 14 optimized for each diseased site, the scanning electromagnet 3 is excited in accordance with each of patterns that vary depending on diseased sites. Accordingly, the BH hysteresis curves on the BH plane, along which the magnetization characteristics of the scanning electromagnet 3 follow, vary depending on the beam paths.

For example, in the case where the scanning electromagnet 3 is excited in a given pattern, the magnetic characteristic of the scanning electromagnet 3 follows the BH hysteresis curves such as thin solid lines 26a and 27a in FIG. 9A and FIG. 9B. Because the particle beam therapy system 51 deals with a human body, the irradiation is stopped when a contingency occurs. The coordinates of a point, on the hysteresis curve, that corresponds to the stop position (stop spot) where the irradiation has been stopped are (P1x, P1y). After that, the irradiation is resumed after the safety is confirmed. When the irradiation is resumed, it is required to resume the irradiation after the condition of the scanning electromagnet 3 at a time when irradiation has not been stopped is reproduced. In order to reproduce the condition of the scanning electromagnet 3, it is required to reproduce the same magnetic flux density B, the same magnetic-field intensity H, and the same magnetic-field vs. time gradient dH/dt. Accordingly, it is effective that before the irradiation of the charged particle beam 1 is started, the scanning electromagnet 3 is initialized, for example, as B=0, H=0, and dH/dt=0, in such a way that the irradiation is always started with the same condition of the scanning electromagnet 3, i.e., in such a way that when the condition of the scanning electromagnet 3 is represented on the BH plane, the BH hysteresis curve always starts from the same point (P1x, P1y). The broken lines 26b and 27b are the BH hysteresis curves at a time when the scanning electromagnet 3 is controlled with irradiation unstopped. The initialization of the scanning electromagnet 3 and the idle operation explained in Embodiment 1 enable the condition of the scanning electromagnet 3 to always start from the same point (P1x, P1y) when represented on the BH plane.

With regard to the initialization of the scanning electromagnet 3, there is given a predetermined excitation pattern, for example, in such a way that the scanning electromagnet 3 is excited up to +H-direction maximum value, which is within the specification range, and then is excited up to −H-direction maximum value, which is within the specification range. By, as described above, exciting the scanning electromagnet 3 up to the maximum values, it can be expected that the residual magnetism in the magnetic material of the scanning electromagnet 3 is eliminated. The initialization of the scanning electromagnet 3 is not limited to the condition in which B=0, H=0, and dH/dt=0; there may exist an offset, as long as the reproducibility can be ensured.

In Embodiment 1, there has been explained an example in which irradiation of the scanning electromagnet 3 is not performed before idle operation. In Embodiment 1, although it is rare, a case may occur in which even during idle operation, the effect of the hysteresis of the scanning electromagnet 3 cannot sufficiently be eliminated. In the case where the effect of the hysteresis of the scanning electromagnet 3 is not sufficiently eliminated, the positional accuracy of beam irradiation may be deteriorated to some extent. However, in Embodiment 2, the scanning electromagnet 3 is initialized before idle operation; therefore, the effect of the hysteresis of the scanning electromagnet 3 can sufficiently be eliminated.

In addition, it is also conceivable that as the method of adjusting the condition of the scanning electromagnet 3, an auxiliary coil is utilized. In the case where the command value for the scanning electromagnet 3 is "0", i.e., in the case where because no driving current is supplied from the scanning electromagnet power source 4, the scanning electromagnet 3 is not excited, the magnetic flux density B should be "0". However, as represented in FIG. 9A and FIG. 9B, in some cases, due to the hysteresis characteristics, the magnetic flux density B does not become "0". In this situation, an electric current is applied to an auxiliary coil provided in the scanning electromagnet 3 so that the condition thereof is controlled, whereby the magnetic flux density B can be made to be "0" in such a way that the residual magnetism is cancelled. Also in such a manner as described above, beam irradiation can be started with the condition of the scanning electromagnet 3 made always the same (for example, the origin on the BH plane or the stop position (P1x, P1y) in FIG. 9A and FIG. 9B). As described above, the initialization of the scanning electromagnet 3 is not limited to the condition in which B=0; there may exist an offset, as long as the reproducibility can be ensured.

Figure 10:
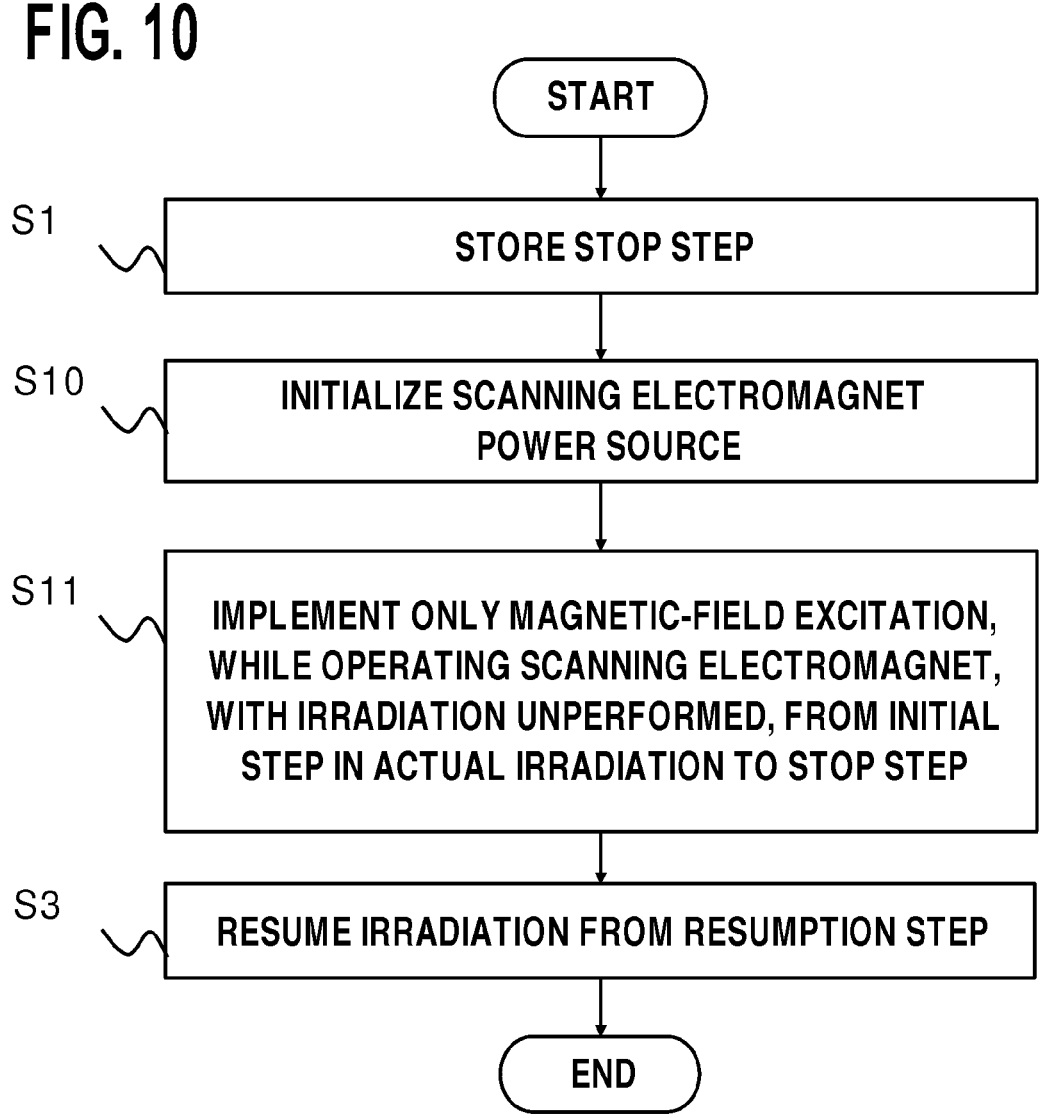
FIG. 10 is a flowchart representing a procedure for stopping and resuming beam irradiation in a particle beam therapy system according to Embodiment 2 of the present invention.

A procedure for stopping and resuming beam irradiation will be explained with reference to FIG. 10. FIG. 10 is a flowchart representing a procedure for stopping and resuming beam irradiation in a particle beam therapy system according to Embodiment 2. The procedure for stopping and resuming beam irradiation according to Embodiment 2 differs from the procedure for stopping and resuming beam irradiation according to Embodiment 1 in that a procedure (the step S10) for initializing the scanning electromagnet 3 is added, and the idle operation where the scanning electromagnet 3 is controlled starts from the initial step in actual irradiation, i.e., from the initial step in the first slice (the step S11: the idle operation procedure).

In the case where a contingency occurs during therapy, the irradiation management apparatus 32 performs the foregoing determination on irradiation stop, based on the interlock signal generated by the interlock information inputting device, and stops the irradiation. The irradiation management apparatus 32 stores the interruption step (the step S1: the stop step storage procedure). The irradiation management apparatus 32 initializes the scanning electromagnet 3 (the step S10: the magnetic-field initialization procedure). The foregoing method can be utilized for initializing the scanning electromagnet 3. After the magnetic-field initialization, the irradiation management apparatus 32 activates the scanning electromagnet power source 4, with a beam unirradiated in the process from the initial step in actual irradiation to the stop step, so as to perform only magnetic-field excitation of the scanning electromagnet 3 (the step S11: the idle operation procedure). As is the case with Embodiment 1, beam irradiation is resumed (the step S3: irradiation start procedure).

By performing idle operation after magnetic-field initialization, the irradiation resumption condition (i.e., the BH hysteresis curve on the BH plane) where $B=B_0$, $H=H_0$, and $dH/dt=H'_0$ can be reproduced. In this regard, however, $B_0$ denotes the magnetic flux density at a time before irradiation interruption; $H_0$ denotes the magnetic-field intensity at a time before irradiation interruption; $H'_0$ denotes the magnetic-field vs. time gradient at a time before irradiation interruption.

As the effect of adopting this sequence, even when irradiation is interrupted halfway, the irradiation can be resumed with the same condition, of the scanning electromagnet 3, that has followed the same BH hysteresis curve; thus, it is made possible to minimize the positional deviation of the irradiation spot. In Embodiment 2, as examples of methods for reproducing the condition, at a time before irradiation interruption, where $B=B_0$, $H=H_0$, $dH/dt=H'_0$, there have been described a method where excitation is carried out up to the maximum level and then is carried out up to the minimum level and a method where an auxiliary coil is utilized; however, there exists no intention to limit the present invention thereto, because the initialization method in which the condition where $B=B_0$, $H=H_0$, $dH/dt=H'_0$ can be reproduced when therapy is resumed has the same effect.

However, the particle beam therapy system 51 according to Embodiment 2 performs magnetic-field initialization before idle operation; therefore, in Embodiment 2, the effect of the hysteresis of the scanning electromagnet 3 can more sufficiently be eliminated than in Embodiment 1.

Figure 11:
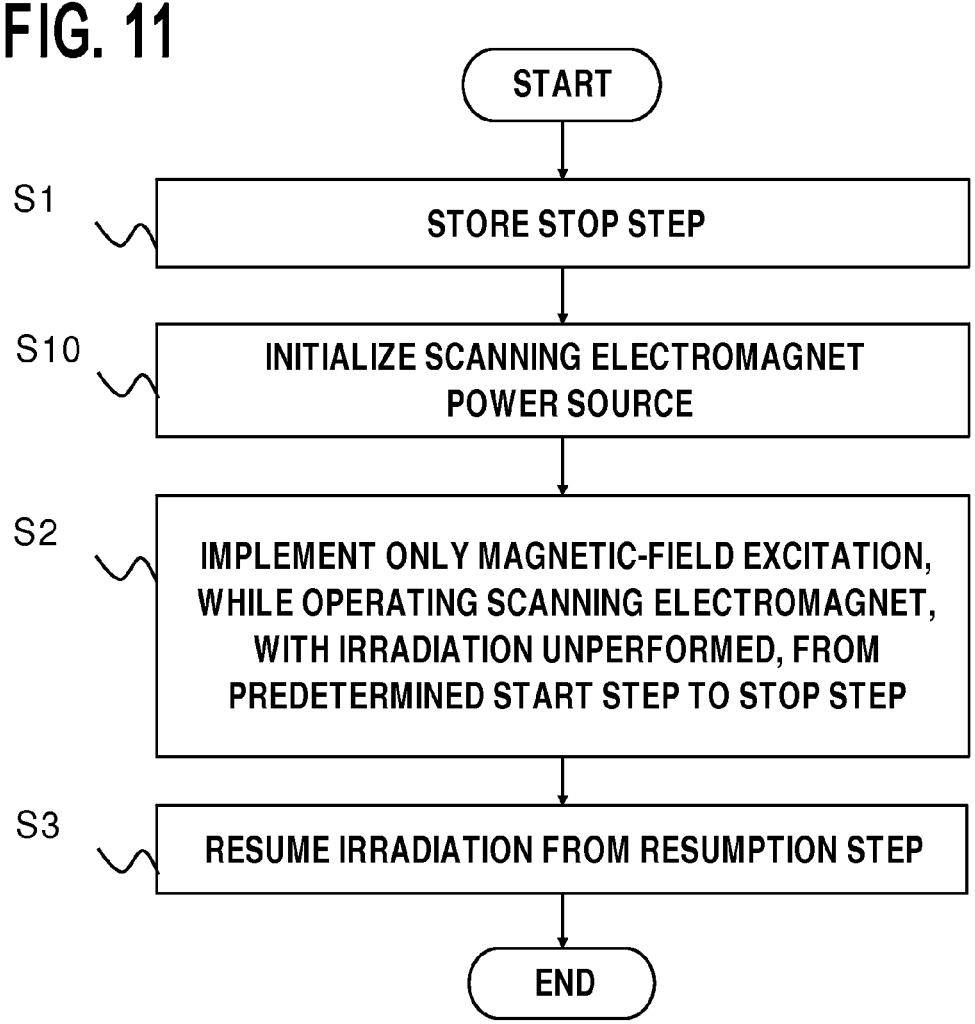
FIG. 11 is a flowchart representing another procedure for stopping and resuming beam irradiation in a particle beam therapy system according to Embodiment 2 of the present invention.

In the case of an irradiation method in which the charged particle beam 1 is stopped when slices are changed and the charged particle beam 1 is continuously irradiated when irradiation is performed within a single and the same slice, it is made possible that a magnetic-field sensor is provided in the scanning electromagnet 3 and through the magnetic-field sensor, the residual magnetism can be measured before a beam is irradiated onto each slice. By preliminarily measuring the residual magnetism, the initialization of the scanning electromagnet 3 can be performed based on the measured value of the residual magnetism, when the initial step in the slice is resumed before the idle operation. Before the idle operation is performed, the initialization of the scanning electromagnet 3 can be performed based on the measured value of the residual magnetism in the initial step in the slice at which the idle operation is started. Because the initialization of the scanning electromagnet 3 can be performed before the idle operation is performed, operation can be implemented from the initial step in the slice at which beam irradiation has been interrupted or from a step that is predetermined steps prior to the stop step. FIG. 11 represents a procedure for stopping and resuming beam irradiation in the foregoing case.

FIG. 11 is a flowchart representing another procedure for stopping and resuming beam irradiation in a particle beam therapy system according to Embodiment 2. FIG. 11 differs from FIG. 10 in that the step S11 has been replaced by the step S2 explained in Embodiment 1. A magnetic-field sensor measures the magnetic field of the scanning electromagnet 3 at the initial desired irradiation position coordinates Pi in each of the slices. The irradiation management apparatus 32 performs initialization processing for the scanning electromagnet 3 based on the measured value of the magnetic field at the initial desired irradiation position coordinates Pi in the slice at which the idle operation is started. In this method, in the case where the irradiation subject 15 is large and hence the number of irradiation steps is large, even when irradiation is interrupted in a latter slice, idle operation is performed not from the initial step in actual irradiation but from the initial step in the slice at which the irradiation has been interrupted; therefore, the time for the idle operation can be reduced.

In Embodiment 1, it has been explained that although in view of the reproducibility, it is desirable to perform the idle operation from the initial step for a given slice, a considerable effect can still be obtained even when the idle operation is performed from a step, empirically confirmed, that is predetermined steps (predetermined spots) prior to the stop step. By utilizing this method, the effect of the hysteresis of the scanning electromagnet 3 can sufficiently be eliminated not only in the case where initialization processing for the scanning electromagnet 3 is performed based on the measured value of the magnetic field at the initial desired irradiation position coordinates Pi in a given slice, but also in the case where the initialization processing for the scanning electromagnet 3 is performed under a predetermined initialization condition, for example, where B=0, H=0, and dH/dt=0; therefore, the irradiation accuracy can fall within an allowable range.

In each of Embodiments 1 and 2, there has been explained an irradiation method in which the charged particle beam 1 is stopped when slices are changed, and the charged particle beam is continuously irradiated when irradiation is performed within a single and the same slice; however, the present invention can be applied to other irradiation methods such as the spot-scanning method in which the charged particle beam 1 is stopped for each irradiation spot and the raster-scanning method.

DESCRIPTION OF REFERENCE NUMERALS

1: charged particle beam
3, 3*a*, 3*b*, 3*x*, 3*y*: scanning electromagnet
7: position monitor
15: irradiation subject
24: patient
32: irradiation management apparatus
51: particle beam therapy system
54: accelerator
78: patient sensor
84, 84*a*, 84*b*: interlock information inputting device
Ia: current correction data
Io, Ir: command current
Pi: desired irradiation position coordinates
Ps: measured position coordinates

The invention claimed is:

1. A particle beam therapy system that irradiates a charged particle beam, accelerated by an accelerator and scanned by a scanning electromagnet, onto a diseased site of a patient, the particle beam therapy system comprising:

an irradiation management apparatus that controls the scanning electromagnet, based on desired irradiation position coordinates of the charged particle beam; and an interlock information inputting device that generates an interlock signal for stopping irradiation of the charged particle beam, when a contingency occurs, wherein the irradiation management apparatus is provided with a command value generator that outputs a control input to the scanning electromagnet; and a stop step storage memory that stores a stop step corresponding to the desired irradiation position coordinates at which irradiation of the charged particle beam stops, when the interlock signal is generated by the interlock information inputting device, and wherein when irradiation of the charged particle beam is resumed, the irradiation management apparatus performs idle operation in which the scanning electromagnet is controlled, with the charged particle beam unirradiated, from a start step, which is situated prior to the stop step and is different from an initial step corresponding to the initial desired irradiation position coordinates in actual irradiation, to the stop step, and then irradiates the charged particle beam from the desired irradiation position coordinates corresponding to the stop step.

2. The particle beam therapy system according to claim 1, wherein the irradiation management apparatus scans the charged particle beam onto respective slices, of the diseased site, that are layers corresponding to kinetic energy levels; and the start step is a step corresponding to the initial desired irradiation position coordinates, in the slice, at which irradiation of the charged particle beam stops.

3. The particle beam therapy system according to claim 2, wherein the interlock information inputting device includes a patient sensor that detects a motion of the patient and a signal generator that generates the interlock signal when a detection signal from the patient sensor exceeds a predetermined range.

4. The particle beam therapy system according to claim 2, wherein the interlock information inputting device includes an irradiation stop button that is pushed when a contingency occurs and a signal generator that generates the interlock signal, based on a signal from the irradiation stop button.

5. The particle beam therapy system according to claim 2, wherein the irradiation management apparatus performs initialization processing for the scanning electromagnet before the idle operation, when irradiation of the charged particle beam is resumed.

6. The particle beam therapy system according to claim 1, wherein the irradiation management apparatus scans the charged particle beam onto respective slices, of the diseased site, that are layers corresponding to kinetic energy levels; and the start step is a step in the slice at which irradiation of the charged particle beam stops and is a step that is situated predetermined steps prior to the stop step.

7. The particle beam therapy system according to claim 6, wherein the interlock information inputting device includes a patient sensor that detects a motion of the patient and a signal generator that generates the interlock signal when a detection signal from the patient sensor exceeds a predetermined range.

8. The particle beam therapy system according to claim 6, wherein the interlock information inputting device includes an irradiation stop button that is pushed when a contingency occurs and a signal generator that generates the interlock signal, based on a signal from the irradiation stop button.

9. The particle beam therapy system according to claim 6, wherein the irradiation management apparatus performs initialization processing for the scanning electromagnet before the idle operation, when irradiation of the charged particle beam is resumed.

10. The particle beam therapy system according to claim 1, wherein the interlock information inputting device includes a patient sensor that detects a motion of the patient and a signal generator that generates the interlock signal when a detection signal from the patient sensor exceeds a predetermined range.

11. The particle beam therapy system according to claim 10, wherein the irradiation management apparatus performs initialization processing for the scanning electromagnet before the idle operation, when irradiation of the charged particle beam is resumed.

12. The particle beam therapy system according to claim 1, wherein the interlock information inputting device includes an irradiation stop button that is pushed when a contingency occurs and a signal generator that generates the interlock signal, based on a signal from the irradiation stop button.

13. The particle beam therapy system according to claim 12, wherein the irradiation management apparatus performs initialization processing for the scanning electromagnet before the idle operation, when irradiation of the charged particle beam is resumed.

14. The particle beam therapy system according to claim 1, wherein the irradiation management apparatus performs initialization processing for the scanning electromagnet before the idle operation, when irradiation of the charged particle beam is resumed.

15. The particle beam therapy system according to claim 14, further including a magnetic-field sensor that measures a magnetic field of the scanning electromagnet,
wherein the irradiation management apparatus scans the charged particle beam onto respective slices, of the diseased site, that are layers corresponding to kinetic energy levels,
wherein the magnetic-field sensor measures a magnetic field of the scanning electromagnet at the initial desired irradiation position coordinates in each of the slices, and
wherein the irradiation management apparatus performs initialization processing for the scanning electromagnet, based on a measured value of the magnetic field at the initial desired irradiation position coordinates in the slice at which the idle operation is started.

16. A particle beam therapy system that irradiates a charged particle beam, accelerated by an accelerator and scanned by a scanning electromagnet, onto a diseased site of a patient, the particle beam therapy system comprising:
an irradiation management apparatus that controls the scanning electromagnet, based on desired irradiation position coordinates of the charged particle beam; and
an interlock information inputting device that generates an interlock signal for stopping irradiation of the charged particle beam, when a contingency occurs,
wherein the irradiation management apparatus scans the charged particle beam onto respective slices, of the diseased site, that are layers corresponding to kinetic energy levels,
wherein the irradiation management apparatus is provided with a command value generator that outputs a control input to the scanning electromagnet; and a stop step storage memory that stores a stop step corresponding to the desired irradiation position coordinates at which irradiation of the charged particle beam stops, when the interlock signal is generated by the interlock information inputting device, and
wherein when irradiation of the charged particle beam is resumed, the irradiation management apparatus performs idle operation in which the scanning electromagnet is controlled, with the charged particle beam unirradiated, from a start step, which is situated prior to a step in the slice at which irradiation of the charged particle beam stops corresponding to the initial desired irradiation position coordinates, to the stop step, and then irradiates the charged particle beam from the desired irradiation position coordinates corresponding to the stop step.

17. The particle beam therapy system according to claim 16, wherein the interlock information inputting device includes a patient sensor that detects a motion of the patient and a signal generator that generates the interlock signal when a detection signal from the patient sensor exceeds a predetermined range.

18. The particle beam therapy system according to claim 16, wherein the interlock information inputting device includes an irradiation stop button that is pushed when a contingency occurs and a signal generator that generates the interlock signal, based on a signal from the irradiation stop button.

19. The particle beam therapy system according to claim 16, wherein the irradiation management apparatus performs initialization processing for the scanning electromagnet before the idle operation, when irradiation of the charged particle beam is resumed.

* * * * *